United States Patent
Kartaeusch et al.

(10) Patent No.: US 11,237,238 B2
(45) Date of Patent: Feb. 1, 2022

(54) METHOD AND DEVICE FOR CONTROLLING A MAGNETIC RESONANCE TOMOGRAPHY SYSTEM FOR MAGNETIC RESONANCE FINGERPRINTING MEASUREMENTS

(71) Applicant: Siemens Healthcare GmbH, Erlangen (DE)

(72) Inventors: Ralf Kartaeusch, Bubenreuth (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 42 days.

(21) Appl. No.: 16/739,466

(22) Filed: Jan. 10, 2020

(65) Prior Publication Data
US 2020/0225304 A1 Jul. 16, 2020

(30) Foreign Application Priority Data
Jan. 10, 2019 (EP) .................................. 19151172

(51) Int. Cl.
*G01V 3/00* (2006.01)
*G01R 33/48* (2006.01)
*G01R 33/54* (2006.01)

(52) U.S. Cl.
CPC ....... *G01R 33/4828* (2013.01); *G01R 33/543* (2013.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 6,289,232 B1 * 9/2001 Jakob ................. G01R 33/5611
324/307
8,784,314 B2 * 7/2014 Mathew ................... A61B 8/00
600/437
(Continued)

FOREIGN PATENT DOCUMENTS

DE 102016204145 A1 9/2017
EP 3382416 A1 10/2018

OTHER PUBLICATIONS

"Quantitative MRI," https://www.nist.gov/programs-projects/quantitative-mri; Oct. 10, 2018.
(Continued)

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

In a method for controlling a magnetic resonance tomography system for a Magnetic Resonance Fingerprinting (MRF) measurement: a dictionary group including at least two dictionaries is provided/created, each of the at least two dictionaries containing a multiplicity of different intensity profiles with a specific sampling scheme; a preliminary recording of magnetic resonance tomography (MRT) measurements is created; a sampling scheme is determined/defined based on the preliminary recording; a dictionary is selected from the at least two dictionaries of the dictionary group based on the preliminary recording; and an MRF
(Continued)

measurement is performed using the defined sampling scheme and an MRF evaluation based on the selected dictionary.

23 Claims, 3 Drawing Sheets

(58) Field of Classification Search
USPC .......................................................... 324/309
See application file for complete search history.

(56) References Cited

U.S. PATENT DOCUMENTS

| | | | |
|---|---|---|---|
| 9,167,240 B1* | 10/2015 | Sevick-Muraca .... | A61B 5/0071 |
| 2011/0043206 A1* | 2/2011 | Kimura ............ | G01R 33/56341 |
| | | | 324/309 |
| 2017/0089995 A1* | 3/2017 | Basser ............... | G01R 33/5608 |
| 2017/0261579 A1 | 9/2017 | Lauer | |
| 2017/0322276 A1* | 11/2017 | Bhat .................. | G01R 33/4835 |
| 2017/0328973 A1* | 11/2017 | Amthor ............. | G01R 33/4828 |
| 2018/0017646 A1* | 1/2018 | Feiweier ............. | G01R 33/561 |
| 2018/0067900 A1* | 3/2018 | Mos .................... | G03F 7/70508 |
| 2018/0292484 A1* | 10/2018 | Hoppe ............. | G01R 33/5614 |

OTHER PUBLICATIONS

Karsten Sommer et al.: "Determination of the Optimum Pattern Length of MRF Sequences"; Proceedings of the International Society for Magnetic Resonance in Medicine; ISMRM; 25th Annual Meeting and Exhibition; Honolulu, HI, USA; Apr. 22-Apr. 27, 2017; No. 1491; Apr. 7, 2017; XP040689059; 2017.

ITIS Foundation, "Tissue Properties—Relaxation Times," https://itis.swiss/virtual-population/tissue-properties/database/relaxation-times/; Oct. 10, 2018.

Gold, Garry E. et.al.; "Musculoskeletal MRI at 3.0 T: Relaxation Times and Image Contrast"; https://www.ajronline.org/doi/pdfplus/10.2214/ajr.183.2.1830343; 2003.

European Search Report dated Jul. 16, 2019, for Application No. 19151172.4.

Arnold, Johannes F. T., Dissertion: "Functional Imaging of Lungs and the Bronchial carcinoma using magnetic resonance imaging", 2007, including English language translation.

* cited by examiner

METHOD AND DEVICE FOR CONTROLLING A MAGNETIC RESONANCE TOMOGRAPHY SYSTEM FOR MAGNETIC RESONANCE FINGERPRINTING MEASUREMENTS

CROSS REFERENCE TO RELATED APPLICATIONS

This patent application claims priority to European Patent Application No. 19151172.4, filed Jan. 10, 2019, which is incorporated herein by reference in its entirety.

BACKGROUND

Field

The disclosure relates to a method and a device for controlling a magnetic resonance tomography system in the context of an MRF measurement, a corresponding controller and a magnetic resonance tomography system ("MRT system"), and a method for producing a magnetic resonance tomography system.

Related Art

Magnetic Resonance Fingerprinting (MRF) has for some time been a very promising new technology for quantitative imaging. When an MRF procedure is performed, an intensity profile is measured over time. The greatest possible dynamic range of the intensity profile for different recordings is generated during a measurement in this case by means of high-frequency pulses with varying flip angles and/or separation in terms of echo time (TE) or repetition time (TR). The order in which the recordings take place with their respective parameter values is referred to as a "sampling scheme". In relation to the activation of an MRT system, the sampling scheme can be considered as the arrangement of signals in a pulse sequence or the order of various pulse sequences.

Individual pixels of images are viewed as part of this activity. Assuming that an image consisting of image dots is recorded multiple times from the same region of a patient using different parameters, those image dots corresponding to a common spatial coordinate of the region are then combined into a group and their intensity profile is viewed across the various recordings. For the sake of clarity, and since stacks of two-dimensional images are often present, these groups of image dots are referred to as "pixels" in the following. This expression "pixel" or "pixel-based" therefore refers not only to an image dot of a single image, but to the group of all image dots in a series of images at a spatial coordinate or image coordinate (which is always identical for each group). If all images in a respective series of images always depict the same region, the same image coordinate corresponds to the same spatial coordinate. Each pixel essentially indicates the state of a point in the patient, which has been recorded using different parameters. A pixel-based intensity profile can therefore generally be considered as an intensity profile at a specific pixel across the series of images. The intensity profile is therefore viewed in a pixel-based manner (using the same spatial coordinate) for all recordings.

Following a Fourier transformation, which is usually executed as a non-uniform FFT (since a heavily under-sampled image is often recorded by means of a spiral trajectory), the intensity profile is compared in a pixel-based manner with entries in a previously simulated "dictionary". In the field of imaging, the English term "dictionary" is also used in German. The dictionary is a collection of simulations of intensity profiles of the tissue with the sampling scheme of the sequence. A multiplicity of values for tissue-specific parameters, e.g. T1 and T2 relaxation times and photon densities, are simulated for the tissue in this case. All of these simulations for various T1 and T2 values then represent the entries in the dictionary. In summary, it can be said that an entry in the dictionary corresponds to an intensity profile which is dependent on the parameters concerned, e.g. tissue-specific parameters, using the specified sampling scheme.

The intensity profile for each pixel is now compared with entries in the dictionary, which largely correspond to various T1 and T2 values, for a series of images. The comparison of the measured intensity profiles with the intensity profiles in the dictionary looks for the closest intensity profile for each pixel. For each pixel-based intensity profile, that entry in the dictionary is therefore used in which the (simulated) intensity profile most closely matches the real intensity profile. The tissue-specific parameters for this intensity profile, e.g. T1 and T2 values, are then saved pixel for pixel in a map.

This is then repeated for further pixels. When this is performed for all pixels, a T1 and T2 map is produced.

The conventional approach involves comparison with a single dictionary and a fixed sampling/excitation scheme which is used because it provided acceptable results in initial experiments.

A very specific sampling scheme of the signal profile is a prerequisite for good differentiation of the various magnetic resonance parameters (MR parameters). In order to achieve this, it is endeavored to vary e.g. TR and TE. The accuracy of the method in this case depends explicitly on the sampling scheme. A serious problem in this case is identifying an optimal scheme, in order to ascertain the tissue-specific MR characteristic variables (e.g. T2, T1 and diffusion) as quickly as possible.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
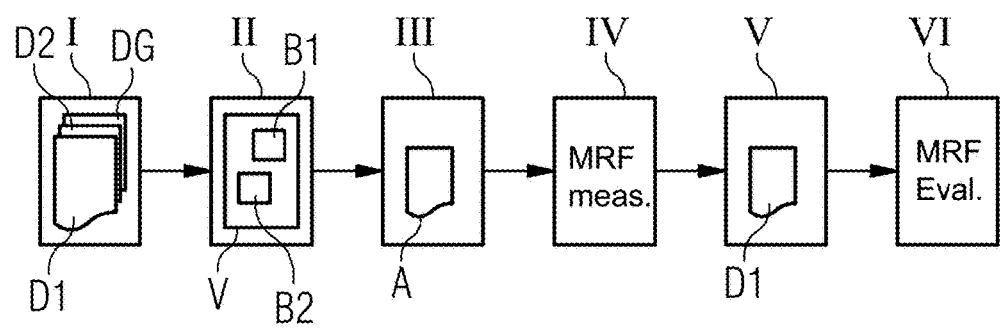
FIG. 1 illustrates a flowchart of a method according to an exemplary embodiment of the disclosure.

The exemplary embodiments of the present disclosure will be described with reference to the accompanying drawings. Elements, features and components that are identical,

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to specify an alternative and more convenient method and a corresponding device, and a controller for controlling a magnetic resonance tomography system in the context of an MRF measurement, and a corresponding magnetic resonance tomography system, by means of which the cited disadvantages can be avoided.

The method and the device according to exemplary embodiments are used to control a magnetic resonance tomography system in the context of an MRF measurement. In particular, they can be provided in the form of components which can be integrated into a magnetic resonance tomography system as supplementary components.

The method according to an exemplary embodiment comprises:

Creating or providing a dictionary group comprising at least two dictionaries, wherein each dictionary contains a multiplicity of different intensity profiles, which correspond to a series of MRT recordings with a specific sampling scheme.

In an exemplary embodiment, the dictionary group includes more than two dictionaries. In an exemplary embodiment, the group includes more than four dictionaries. In an exemplary embodiment, these dictionaries are created specifically for different body regions. As entries, each dictionary comprises said intensity profiles, all of which are recorded with the same sampling scheme within a dictionary. In an exemplary embodiment, different dictionaries may be based on the same sampling scheme (but e.g. different parameters of interest (T1, T2) or different parameter values), but at least two dictionaries in the dictionary group are based on different sampling schemes.

A sampling scheme represents the order of the recordings relative to time with the relevant variation of the recording parameters (see above: flip angle, TE, TR, etc.). The variation can theoretically be marginal (at least by section), such that the same parameter value is used repeatedly. In an exemplary embodiment, a variation of parameters is implemented for an optimal evaluation, such that a clearly measurable variation in the intensity of a pixel can be measured across the different recordings. Within an applicable range of the parameter values, it is advantageous to provoke the greatest possible fluctuation in the intensity. A wide dynamic range of the intensity profile results in an optimal comparability with entries in a dictionaries. In comparison with the previous recording, it is possible to change just a single parameter, but also two or more parameters, in a subsequent recording.

In an exemplary embodiment, a dictionary contains information about the sampling scheme on which these entries are based. However, the respective sampling scheme can also be otherwise associated with the dictionary, e.g. by means of a reference, a link or a code. Information about the sampling scheme can also be associated with an address of the dictionary in the dictionary group. The main point is that by selecting a dictionary from the dictionary group, the specific sampling scheme of the selected dictionary can also be determined.

A sampling scheme is therefore specific to each dictionary, wherein all entries are however based on the same sampling scheme within a dictionary. The disclosure makes use of the fact that different sampling schemes can be applied with different degrees of effectiveness for the various parameters of interest (e.g. T1 and T2) in different body regions.

Preparing a preliminary recording of MRT measurements. These MRT measurements may be configured simply such that the parameter scope can be indicated, but they may also comprise a plurality of MRT recordings with varying recording parameter values. This preliminary recording is also referred to as a "prescan". The preliminary recording is performed before the actual MRF measurement, in order to determine the distribution of the parameter values of interest (e.g. T2 and T1 values) in the desired body region.

The preliminary recording can be e.g. a measurement which as quickly as possible provides an overview of the parameter scope (e.g. minimum and maximum) of the examination object-specific parameters of interest, e.g. the contrasts recorded (e.g. T1 and T2). Non-quantitative MR methods can have a weighting according to a desired contrast, e.g. a T1 weighting or T2 weighting. The contrast in this case can be adjusted to a specific parameter scope, a value range, of the respective tissue-specific parameter. It is therefore also possible to draw conclusions about parameter values that are present in the examined object from a non-quantitative preliminary recording.

Since the value range is known as a result of the preliminary recording, it is then possible selectively to use an optimal dictionary (with its corresponding sampling scheme and/or with a suitable value range of the required parameters in the intensity profiles contained in the dictionary).

Determining and defining a sampling scheme on the basis of the preliminary recording and selecting a dictionary from the dictionary group on the basis of the preliminary recording.

The definition of a sampling scheme can result directly from the preliminary recording in this case, but also after a dictionary is selected from the dictionary group according to the sampling scheme of the selected dictionary. If the sampling scheme takes place before the selection of the dictionary, it is theoretically possible for the MRF measurement likewise to take place before selection of the dictionary but after definition of the sampling scheme, since the MRF measurement is performed using the defined sampling scheme. The dictionary must be selected at the latest before the evaluation of the MRF measurement. (The evaluation of the MRF measurement makes use of the dictionary.)

In an exemplary embodiment, the selection of a dictionary takes place on the basis of a comparison of the results of the preliminary recording with the intensity profiles of a specific prescan dictionary. Intensity profiles can be specifically compared in this case. However, the previously cited parameter scope of the recorded contrasts can also be the deciding factor in the selection.

The definition of the sampling scheme can be effected on the basis of the parameter scope of the recorded contrasts and/or from an intensity profile.

The preliminary recording may be a low-resolution MRF measurement with few repetitions, which is associated with a special prescan dictionary. For example, a normal MRF recording comprises 1,000 to 3,000 repetitions per slice. A preliminary recording may comprise e.g. only 200 repetitions.

For example, the value range of the characteristic variables (and therefore also the parameter scope) is clearly dependent on the body region or tissue to be examined, as illustrated in the following table:

TABLE 1

| Body region | T2 | T1 |
|---|---|---|
| Brain | 60-90 ms | 800-1400 ms |
| Lungs | <1 ms | 800-1400 ms |
| Liver | 35 ms | 800 ms |
| Muscle | 30 ms | 1400 ms |

Assuming four dictionaries, one each for brain, lungs, liver and muscle, it is therefore possible to select a dictionary on the basis of maxima and minima of the T1 and T2 values. It is also possible to create further (sub)dictionaries for each body region, these being optimized in terms of e.g. typical T1 and T2 parameter spectra for specific diseases. The sampling scheme can be defined in exactly the same way. The selection or definition can take place automatically and/or manually.

Performing an MRF measurement using the defined sampling scheme and MRF evaluation on the basis of the selected dictionary. As explained above, the sampling scheme can be defined independently of the dictionary. However, selection of a dictionary also specifies the sampling scheme which must be used for the recordings of the MRF measurement, in order that the intensity profiles of the pixels of the recorded images are comparable with those of the selected dictionary.

It is therefore strongly recommended to make the recordings of the MRF measurement with the sampling scheme, rather than to arrange them consecutively in the scheme later (even if this is actually possible), since the recordings of the images are often not (basically never) independent of each other. In such a recording process, the image number also corresponds to the temporal order of the recordings and allows the time point in the acquisition scheme to be inferred.

The method according to an exemplary embodiment is not only suitable for T2/T1 parameter optimizations, but can also be applied to the optimization of other parameters such as proton density, diffusivity, magnetization transfer, etc.

A MRF processor, according to an exemplary embodiment of the disclosure, for controlling a magnetic resonance tomography system in the context of an MRF measurement comprises:

A dictionary group generator which is designed to create a dictionary group and/or a data interface for the receipt of a supplied dictionary group, wherein the dictionary group comprises at least two dictionaries, wherein each dictionary contains a multiplicity of different intensity profiles of image dots from a series of MRT recordings with a specific sampling scheme.

A preliminary recorder which is designed to prepare a preliminary recording of MRT measurements. These MRT measurements may be configured simply such that the parameter scope can be indicated, but they may also comprise a plurality of MRT recordings with varying recording parameter values.

A determiner which is designed to determine and define a sampling scheme on the basis of the preliminary recording.

A selector which is designed to select a dictionary from the dictionary group on the basis of the preliminary recording.

An evaluator which is designed to perform an MRF measurement using the defined sampling scheme and MRF evaluation on the basis of the selected dictionary.

A controller, according to an exemplary embodiment of the disclosure, for controlling a magnetic resonance tomography system is configured to perform a method according to the disclosure and/or comprises a device (MRF processor) according to the disclosure.

A magnetic resonance tomography system according to an exemplary embodiment of the disclosure comprises a controller according to the disclosure.

A method according to an exemplary embodiment of the disclosure for producing a magnetic resonance tomography system (in particular according to the disclosure) comprises:
setting up the magnetic resonance tomography system,
providing a number of reference phantoms in the magnetic resonance tomography system,
preparing a multiplicity of MRT recordings from the number of reference phantoms with varying recording parameters,
creating a plurality of dictionaries of pixel-based intensity profiles of the MRT recordings, wherein the same sampling scheme is used in each case for a dictionary,
saving the plurality of dictionaries as a dictionary group in a data store of the magnetic resonance tomography system, together with information for each dictionary indicating which sampling scheme was used, wherein information indicating the intended examination region of the dictionary is also saved together with a dictionary.

In the context of the production of dictionaries, these can be derived from actual measured values (e.g. at reference targets). However, in an exemplary embodiment, the dictionaries are also simulated or an optimal dictionary is identified on the basis of a simulation.

In an exemplary embodiment, one or more of the components of the MRF processor or of the controller cited above can be realized wholly or partly in the form of software modules in a processor of a corresponding device or controller. In an exemplary embodiment, a largely software-based realization has the advantage that even devices or control entities already in use can easily be upgraded by means of a software update in order to work in the inventive manner. In this respect, the object is also achieved by a corresponding computer-program-product with a computer program which can be loaded directly onto a computing system or a storage entity of a controller of a magnetic resonance tomography system, comprising program sections for executing all steps of the inventive method when the program is executed on the computing system or the controller. Such a computer program product can optionally comprise, in addition to the computer program, additional elements such as e.g. documentation and/or additional components including hardware components such as e.g. hardware keys (dongles etc.) for using the software.

For the purpose of transportation to the computing system or to the controller and/or for the purpose of storage on or in the computing system or the controller, use may be made of a computer-readable medium, e.g. a memory stick, a hard disc or other transportable or built-in data medium on which are stored the program sections of the computer program that can be read in and executed by a computing system or processor circuitry of the controller. The processor circuitry may comprise e.g. one or more interworking microprocessors or similar for this purpose.

Further particularly advantageous embodiments and developments of the disclosure are derived from the dependent claims and from the following description, wherein the claims in one statutory class of claim can also be developed in a similar manner to the claims and description parts in another statutory class of claim and, in particular, individual features of different exemplary embodiments or variants can also be combined to form novel exemplary embodiments or variants.

In an exemplary embodiment, the preliminary recording is a low-resolution mapping sequence, a specifically optimized MRF trajectory with low spatial and/or temporal resolution or a relaxometry measurement, preferably without local resolution. Such a preliminary recording requires a few seconds in comparison with several minutes for the MRF measurement. As regards the preliminary recording, e.g. the spatial resolution, the preliminary recording is configured in such a way that the measuring time is shorter than the actual MRF measurement by a factor of at least five for the same recording region.

In a method according to an exemplary embodiment, the determination of the sampling scheme is based on the parameter scope of the contrasts recorded during the preliminary recording. This is described in greater detail above. For this, the parameter scope, e.g. the minimum and the maximum, of the examination object-specific parameters is determined, e.g. from the recorded contrasts. As shown in Table 1, the parameter scopes vary considerably during the recording of different body regions. If a specific sampling scheme is available for a specific range of parameter scopes, said sampling scheme is determined and defined for the MRF measurement. If no such sampling scheme is available, then that sampling scheme in which the parameter scopes are closest to those determined is defined for the MRF measurement. It is however alternatively or additionally possible to output a message that no suitable sampling scheme could be determined.

In a method according to an exemplary embodiment, in the context of a recording (for the MRF measurement in particular), one or more of the following recording parameters are varied for a plurality of MRT recordings according to the defined sampling scheme:
flip angle,
phase of the flip angle,
echo time,
repetition time,
echo train (e.g. number of echoes),
number of recorded images in a series of images, and/or partial Fourier factor/trajectory.

In an exemplary embodiment, the preliminary recording is configured such that an overview of the parameter scope of the dictionaries in the dictionary group is obtained in respect of the recorded contrasts. Since the dictionaries have normally been recorded with different sampling schemes which allow for the parameter scope of the examination object-specific parameters (e.g. T1 and T2) for measurements at the different body regions, it is advantageous for the preliminary measurement to cover the whole range of parameter scopes from all dictionaries. In an exemplary embodiment, the preliminary measurement is so configured in this case as to comprise measurements at least in the region of the limits of all parameter scopes of the individual dictionaries. In this way, it is advantageously possible to decide which sampling scheme (possibly of a dictionary) should be used for the MRF measurement.

In a method according to an exemplary embodiment, a manual selection by a user is performed in order to define the sampling scheme and/or select the dictionary. In an exemplary embodiment, this selection option is available in addition to an automatic definition of the sampling scheme and/or selection of the dictionary. For example, an overview of the preliminary measurement together with an overview of the dictionaries in the dictionary group and/or an overview of the available sampling schemes can be output via a computer terminal and a desired dictionary and/or the desired sampling scheme can be selected by a user. In the case of experienced operators in particular, it is advantageous for the operator to be able to effect a manual selection of the sampling scheme or the dictionary.

In a method according to an exemplary embodiment, two types of sampling schemes can be defined for at least one type of MRF measurement. That is, in an exemplary aspect, both sampling schemes can be used for the respective MRF measurement and that both can be used for the comparison of the measured data with the same dictionary. In this case, one type of sampling scheme has a higher resolution than the other type of sampling scheme, and the other type of sampling scheme allows faster data recording than the first type of sampling scheme. Therefore both a "high-resolution" recording option and a rapid recording option are available for the comparison of measured data with entries in a dictionary.

The same applies to dictionaries. In a method according to an exemplary embodiment, two types of dictionaries can be defined for at least one type of MRF measurement. By this is meant that both dictionaries can be used for the respective MRF measurement. In this case, one type of dictionary has a higher resolution than the other type of dictionary, and the other type of dictionary allows faster data recording than the first type of dictionary. Therefore both a "high resolution" dictionary and a dictionary for rapid recording are available.

For example, provision is made for sampling schemes and/or dictionaries of which some are optimized for high T2/T1 resolution and others are optimized for rapid data recording with reduced accuracy. It is therefore possible, particularly in the case of a limited T1 or T2 value range, either to reduce the measuring time required to record the trajectory or to increase the resolution of the sampled value range and maintain the same measuring time. Furthermore, a reduced T1 or T2 value range is accompanied by a reduced reconstruction time for the comparison of the trajectory with the dictionary entries.

In a method according to an exemplary embodiment, different dictionaries and/or different sampling schemes are used for different body regions and/or examinations. These dictionaries or sampling schemes are optimized in relation to the respective body regions or examinations in this case. In an exemplary embodiment, parameter scopes and/or contrasts and/or specific variations of parameter values are applied as part of a sampling scheme according to the body region or examination.

In a method according to an exemplary embodiment, after providing a dictionary group and before the MRF measurement, an additional dictionary with an individual sampling scheme is created. Although this is costly in terms of time, it can nonetheless be advantageous if a patient exhibits values which deviate from the norm (e.g. abnormal parameter scopes) in the region to be examined, e.g. due to pathologies such as a vascularized or non-vascularized tumor or calcification. Such pathologies can result in relaxation times which deviate from the typical values.

In a method according to an exemplary embodiment, specific sampling schemes are determined for the purpose of creating the dictionary group for different examination regions by means of measurements. In an exemplary embodiment, alternatively or additionally, for an examination region, a specific choice of parameter scopes is made for this examination region.

In a method according to an exemplary embodiment, a reference phantom is used for the purpose of creating a plurality of dictionaries in a dictionary group. In an exemplary embodiment, the reference phantom is a National Institute of Standards and Technology (NIST) phantom. In an exemplary embodiment, the following additional steps are performed as part of this method. In an exemplary embodiment, these additional steps are performed in advance of the MRF measurement or as part of the setup or calibration of the MRT system. In an exemplary embodiment, the steps includes:

Providing the reference phantom in a magnetic resonance tomography system. The reference phantom should allow the simulation of various body regions in this case.

Preparing a multiplicity of MRT recordings from the reference phantom with varying recording parameters. In an exemplary embodiment, these varying recording parameters comprise varied flip angle, echo time, partial Fourier factors/trajectories, varied repetition time (TR) train or echo train.

Automatically ascertaining the difference between the known reference values of the reference phantom and measured values of the MRT recordings.

Ascertaining the mean value and the standard deviation of the measured values. These are used to optimize the sampling scheme. It is endeavored in this case to minimize the difference ascertained above. The MRF measurement produces e.g. T1 and T2 maps from a similarity comparison of the intensity profile.

Evaluating the measurements for the body regions to be optimized, using suitable regions of the reference phantom for this purpose. The reference phantom provides a broad bandwidth of T1 and T2. In an exemplary embodiment, if only specific value ranges are important for a body region, the minimization of the difference only takes place in the relevant parts.

In a method according to a further exemplary embodiment, a simulation of intensity profiles is performed for the purpose of creating a plurality of dictionaries of a dictionary group. In an exemplary embodiment, this simulation also allows for the artifact and image quality aspects such as e.g. noise or undersampling. In an exemplary embodiment, an optimal sampling scheme is identified for various T1 and T2 ranges, i.e. a sampling scheme which exhibits least deviations from the references. In an exemplary embodiment, a simulation is based on simulated MRT mappings. In an exemplary embodiment, the intensity profiles are simulated by a Bloch simulation in a similar way to the creation of the dictionaries.

The described enhancement with adapted acquisition is a means of extending MRF to broad regions of the human or animal body. The adaptation to a value range allows the measurement to be performed more quickly. For example, the number of echoes or the TR train is reduced according to region. The accuracy of the measurement is also increased (T1 and T2 are ascertained more precisely).

By virtue of ascertaining the sampling scheme automatically, it is possible at little expense to identify a solution which is optimized for a predetermined body region.

FIG. 1 shows a flow diagram for a possible flow of a method according to the disclosure for controlling a magnetic resonance tomography system in the context of an MRF measurement.

In step I, a dictionary group DG comprising at least two dictionaries D1, D2 is provided, wherein each dictionary D1, D2 contains a multiplicity of different intensity profiles (see FIG. 2) for a series of MRT recordings B1, B2 with a specific sampling scheme A. The dictionary contains intensity profiles to which a T1+T2 and optionally further parameters are assigned.

This step also allows the creation of a dictionary group DG. This however takes a very long time and should therefore be performed at a time when no other measurements are being performed, e.g. at night before a measurement or even during the setup or assembly of the respective magnetic resonance tomography system 1 (see FIG. 3) or alternatively delegated to a computing cluster.

In step II, a preliminary recording V is prepared. These MRT measurements may be configured simply such that the parameter scope can be indicated, but they may also comprise a plurality of MRT recordings B1, B2 with varying recording parameter values.

In step III, a sampling scheme A is determined and defined on the basis of the preliminary recording V.

In step IV, an MRF measurement is performed using the defined sampling scheme A.

In step V, a dictionary D1 is selected from the dictionary group DG on the basis of the preliminary recording V. In the method illustrated here, the definition of the sampling scheme A and the selection of the dictionary D1 take place at different times. It should however be noted that the sampling scheme A and the dictionary D1 go together, i.e. the entries in the dictionary D1 are based on the sampling scheme A.

In step VI, an MRF evaluation is performed on the basis of the selected dictionary D1.

Figure 2:
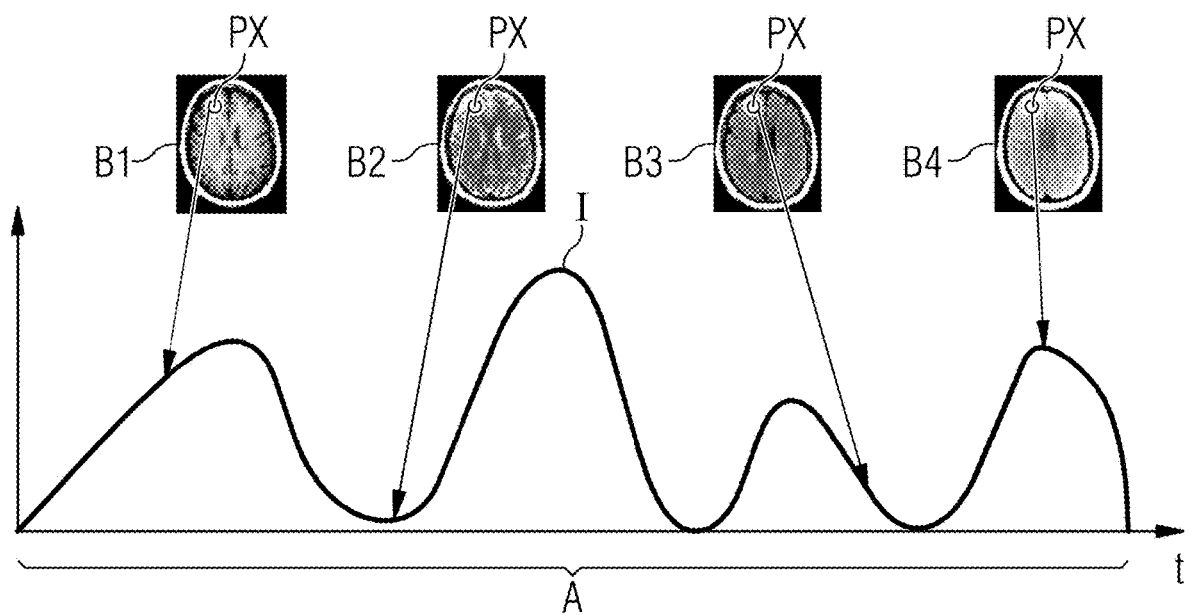
FIG. 2 illustrates an intensity profile according to an exemplary embodiment of the disclosure.

FIG. 2 shows an exemplary intensity profile I plotted over the time axis t, which can be produced during the recording of MRT recordings B1, B2, B3, B4 with a specific sampling scheme A. Such an intensity profile I is measured during an MRF measurement. The entries in the dictionaries D1, D2 are just such intensity profiles I, having been measured at e.g. a reference target and being associated in terms of data with a specific result, e.g. a specific tissue type. A pixel PX is marked (circle) on each of the MRT recordings B1, B2, B3, B4, and always marks the same spatial point in the object (a head here). Since all images show the same region, the pixel PX is also always situated at the same image coordinates. The different intensities of the corresponding pixels PX in the various MRT recordings B1, B2, B3, B4 result in the intensity profile I.

Figure 3:
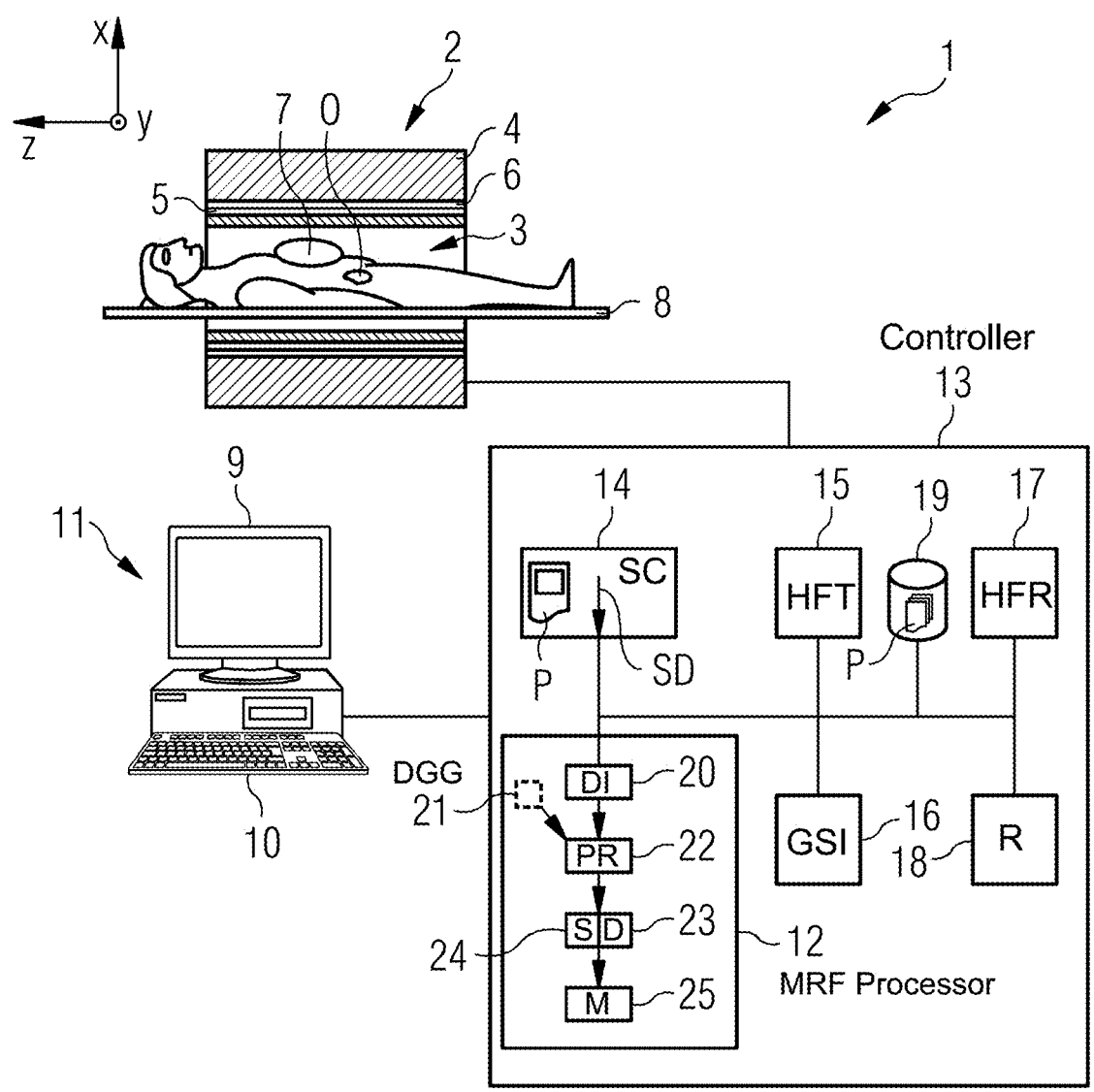
FIG. 3 illustrates a magnetic resonance tomography system according to an exemplary embodiment of the disclosure.

FIG. 3 is a simple schematic illustration of a magnetic resonance tomography system 1. This comprises firstly the actual magnetic resonance scanner 2 with an examination chamber 3 or patient tunnel in which a patient or subject is positioned on a couch 8, the actual examination object O, also referred to as the "examination region" 0, being located in the body of the patient or subject.

The magnetic resonance scanner 2 is normally equipped with a basic field magnetic system 4, a gradient system 6, and an HF transmitting antenna system 5 and an HF receiving antenna system 7. In the exemplary embodiment shown, the HF transmitting antenna system 5 is a whole body coil which is permanently installed in the magnetic resonance scanner 2, whereas the HF receiving antenna system 7 consists of local coils to be arranged on the patient or subject (indicated by a single local coil in the figure). It is however theoretically possible to use the whole body coil as an HF receiving antenna system and the local coils as an HF transmitting antenna system, provided these coils can each be switched into different operating modes. The basic field magnetic system 4 is configured here in a conventional manner so as to generate a basic magnetic field in a longitudinal direction of the patient, i.e. along the longitudinal axis of the magnetic resonance scanner 2 running in a z-direction. As usual, the gradient system 6 comprises gradient coils which can be activated individually, such that gradients can be switched independently of each other in x, y or z-direction.

The magnetic resonance tomography system illustrated in FIG. 3 is a whole-body facility with a patient tunnel into which a patient can be fully introduced. In principle, the disclosure can however also be used for other magnetic resonance tomography systems, e.g. with a C-shaped housing that opens to the side. The only requirement is that corresponding recordings of the examination object O can be prepared.

The magnetic resonance tomography system 1 also has a central controller 13 which is used to control the MR system 1. This central controller 13 comprises a sequence controller 14. This controls the series of high-frequency pulses (HF pulses) and gradient pulses, depending on a selected pulse sequence PS or on a series of multiple pulse sequences, for the purpose of recording a plurality of slices in a relevant region of interest for the examination object within a measuring session. Such a pulse sequence PS can be specified and parameterized within a measurement protocol or control protocol P, for example. Various control protocols P for different measurements or measuring sessions are usually stored in a memory storage unit (memory) 19 and can be selected (and changed if necessary) by an operator and then used to perform the measurement. In the present case, control protocols exist for recording a multiplicity of MRT recordings B1, B2, B3, B4 with varied recording parameters.

For the purpose of outputting the individual HF pulses of a pulse sequence PS, the central controller 13 has a high-frequency transmitter (HFT) 15 by means of which the HF pulses are generated, amplified and fed into the HF transmitting antenna system 5 via a suitable interface (not shown in detail). For the purpose of controlling the gradient coils of the gradient system 6, the controller 13 has a gradient system interface (GSI) 16 in order to switch the gradient pulses correctly according to the specified pulse sequence PS.

The controller 13 also has a high-frequency receiver (HFR) 17 (which likewise communicates in an appropriate manner with the sequence controller 14), in order to receive magnetic resonance signals within the readout windows specified by the pulse sequence PS and as coordinated by the HF receiving antenna system 7, and thereby to acquire the raw data.

A reconstructor 18 then receives the acquired raw data and reconstructs MRT recordings B1, B2, B3, B4 therefrom. This reconstruction likewise is usually effected on the basis of parameters, which can be specified in the respective measurement protocol or control protocol P. This image data can then be saved in a memory 19, for example.

The specific manner in which suitable raw data can be acquired by emitting HF pulses and switching gradient pulses, and in which MR images or parameter maps can be reconstructed therefrom, is generally known to a person skilled in the art and is therefore not explained in further detail here.

The controller 13 of the illustrated magnetic resonance tomography system 1 comprises a Magnetic Resonance Fingerprinting (MRF) processor 12. This MRF processor 12 comprises a data interface 20 for receiving a prepared dictionary group DG (see FIG. 1). The MRF processor 12 can also optionally comprise a dictionary group generator 21 which is designed to create a dictionary group DG. The MRF processor 12 further comprises a preliminary recorder 22 which is designed to prepare a preliminary recording V of MRT measurements comprising a plurality of MRT recordings B1, B2, B3, B4 (see FIG. 2) with varying recording parameter values, a determiner 23 which is designed to determine and define a sampling scheme A on the basis of the preliminary recording V and a selector 24 which is designed to select a dictionary D1, D2 from the dictionary group DG on the basis of the preliminary recording V, and an evaluator (e.g. MRF evaluator) 25 which is designed to perform an MRF measurement using the defined sampling scheme A and an MRF evaluation on the basis of the selected dictionary D1, D2. The evaluator 25 here is a separate unit, which can control the other components of the controller 13 accordingly. However, it can also be realized using the existing components of the controller 13.

Operation of the central controller 13 can be effected via a terminal 11 comprising an input 10 and a display 9, by means of which it is therefore also possible for an operator to operate the whole magnetic resonance tomography system 1. The display 9 can also be used to display magnetic resonance tomography images, and the input 10 (possibly in combination with the display 9) can be used to plan and initiate measurements and in particular to select and optionally modify control protocols P.

The inventive magnetic resonance tomography system 1 and in particular the controller 13 may additionally comprise a multiplicity of further components which are not individually illustrated here but are normally present in such facilities, e.g. a network interface in order to connect the entire system to a network and allow the exchange of raw data and/or image data or parameter maps, as well as other data such as e.g. patient-related data or control protocols.

The manner in which suitable raw data can be acquired by emitting HF pulses and generating gradient fields, and in which magnetic resonance tomography images can be reconstructed therefrom, is generally known to a person skilled in the art and is not explained in further detail here. All manner of measuring sequences such as e.g. EPI measuring sequences or other measuring sequences for generating diffusion-weighted images are likewise generally known to a person skilled in the art.

Figure 4:
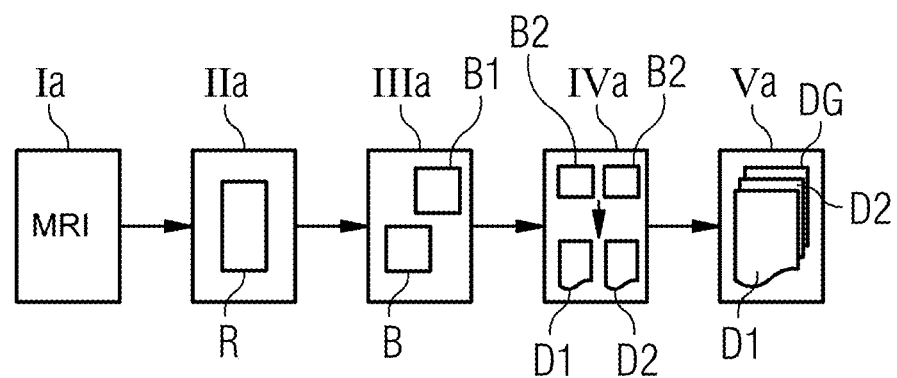
FIG. 4 illustrates flowchart of a method for the production of a magnetic resonance tomography system according to an exemplary embodiment of the disclosure.

FIG. 4 shows a method for producing a magnetic resonance tomography system according to an exemplary embodiment.

In step Ia, a magnetic resonance tomography system 1 is set up as illustrated in FIG. 1, for example. This magnetic resonance tomography system comprises a dictionary group generator 21 which is designed to create a dictionary group DG as described above.

In step IIa, a number of reference phantoms R are provided in the magnetic resonance tomography system 1.

In step IIIa, a multiplicity of MRT recordings B1, B2, B3, B4 are prepared from the number of reference phantoms R with varying recording parameters.

In step IVa, a plurality of dictionaries D1, D2 of pixel-based intensity profiles I of the MRT recordings B1, B2, B3, B4 are created, wherein the same sampling scheme A is used in each case for a dictionary D1, D2.

In step Va, the plurality of dictionaries D1, D2 is saved as a dictionary group DG in a data store 19 of the magnetic resonance tomography system 1, together with information for each dictionary D1, D2 indicating which sampling scheme A was used.

Figure 5:
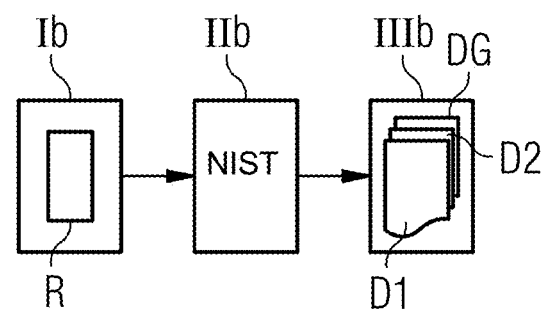
FIG. 5 illustrates a flowchart of a method to create a dictionary group according to an exemplary embodiment of the disclosure.

FIG. 5 shows a method for creating a dictionary group according to an exemplary embodiment.

In step Ib, a NIST phantom R is loaded into the magnetic resonance tomography system 1 (see FIG. 3) as a reference phantom R, and an MRF measurement is performed e.g. overnight with varying flip angle, TE, TR train or echo train and partial Fourier factor/trajectory.

In step IIb, differences between the known values of the NIST phantom R and the measured values are ascertained. The values of the NIST phantom R are known precisely in advance. The difference can be ascertained automatically by means of simple comparison subsequently. Aside from the noise, the individual elements (spheres) of the NIST phantom R deliver constant values.

A good measure for statistical processing of the differences here is the mean value and the standard deviation. The T2 and T1 values of the NIST phantom cover a wide range.

In step IIIb, for the assessment of individual T2 and T1 ranges, only those spheres with T1 and T2 values that are of interest for the respective region are then evaluated, and dictionaries D1, D2 are created from the different configurations of the evaluation.

In conclusion, it is again noted that the method described in detail above and the magnetic resonance tomography system 1 illustrated here are merely exemplary embodiments which can be modified in all manner of ways by a person skilled in the art without thereby departing from the scope of the region. Furthermore, use of the indefinite article "a" or "an" does not exclude multiple occurrences of the features concerned. Likewise, the terms "unit" and "module" do not exclude the possibility that the components concerned may consist of multiple interworking subcomponents, which may also be spatially distributed if applicable.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for controlling a magnetic resonance tomography system for a Magnetic Resonance Fingerprinting (MRF) measurement, the method comprising:
    creating or providing a dictionary group including at least two dictionaries, each of the at least two dictionaries containing a multiplicity of different intensity profiles with a specific sampling scheme;
    preparing a preliminary recording of magnetic resonance tomography (MRT) measurements;
    determining and defining a sampling scheme based on the preliminary recording;
    selecting a dictionary from the at least two dictionaries of the dictionary group based on the preliminary recording; and
    performing an MRF measurement using the defined sampling scheme and an MRF evaluation based on the selected dictionary.

2. The method as claimed in claim 1, wherein the preliminary recording is a relaxometry measurement, a low-resolution mapping sequence or a specially optimized MRF trajectory with low spatial resolution.

3. The method as claimed in claim 1, wherein:
the determination of the sampling scheme is based on a parameter scope of contrasts recorded during the preliminary recording;
the preliminary recording is configured such that an overview of parameter scopes of the at least two dictionaries in the dictionary group is obtained in respect of the recorded contrasts; or
one or more of the following recording parameter values are varied for a plurality of MRT recordings according to the defined sampling scheme: flip angle, phase of the flip angle, echo time, repetition time, echo train, number of recorded images in a series of images and partial Fourier factor/trajectory.

4. The method as claimed in claim 1, wherein:
the determination of the sampling scheme is based on a parameter scope of contrasts recorded during the preliminary recording;
the preliminary recording is configured such that an overview of parameter scopes of the at least two dictionaries in the dictionary group is obtained in respect of the recorded contrasts; and
one or more of the following recording parameter values are varied for a plurality of MRT recordings according to the defined sampling scheme: flip angle, phase of the flip angle, echo time, repetition time, echo train, number of recorded images in a series of images and partial Fourier factor/trajectory.

5. The method as claimed claim 1, wherein defining the sampling scheme comprises a manual user selection to define the sampling scheme and/or select the dictionary.

6. The method as claimed in claim 1, wherein defining the sampling scheme comprises: an automatic definition of the sampling scheme and/or selection of the dictionary.

7. The method as claimed claim 6, wherein defining the sampling scheme further comprises a manual user selection to define the sampling scheme and/or select the dictionary.

8. The method as claimed in claim 1, wherein:
two sampling scheme types and/or two dictionary types are definable for at least one type of MRF measurement;
a first of the sampling scheme types has a higher resolution than a second of the sampling scheme types, and the second of the sampling scheme types allows faster data recording than the first of the sampling scheme types; or
a first of the dictionary types has a higher resolution than a second of the dictionary types, and the second of the dictionary types allows faster data recording than the first of dictionary types.

9. The method as claimed in claim 1, wherein:
two sampling scheme types and/or two dictionary types are definable for at least one type of MRF measurement;
a first of the sampling scheme types has a higher resolution than a second of the sampling scheme types, and the second of the sampling scheme types allows faster data recording than the first of the sampling scheme types; and
a first of the dictionary types has a higher resolution than a second of the dictionary types, and the second of the dictionary types allows faster data recording than the first of dictionary types.

10. The method as claimed in claim 1, wherein different of that at least two dictionaries and/or different ones of the sampling schemes are used for different body regions and/or examinations.

11. The method as claimed in claim 1, further comprising: creating an additional dictionary with an individual sampling scheme after the dictionary group is created or provided, and before the performance of the MRF measurement.

12. The method as claimed in claim 1, wherein the creating of the dictionary group comprises determining specific sampling schemes for different examination regions using measurements, wherein, for each of the examination regions, a specific choice of parameter scopes is made.

13. The method as claimed in claim 1, wherein creating or providing the dictionary group including the plurality of dictionaries comprises: simulating intensity profiles and/or using a reference phantom.

14. The method as claimed in claim 13, wherein the reference phantom is a National Institute of Standards and Technology (NIST) phantom.

15. The method as claimed in claim 13, wherein creating or providing the dictionary group comprises:
providing the reference phantom in a magnetic resonance tomography system;
preparing a multiplicity of MRT recordings from the reference phantom with varying recording parameters;
automatically ascertaining a difference between known reference values of the reference phantom and measured values of the MRT recordings;
ascertaining a mean value and a standard deviation of the measured values of the MRT recordings; and
evaluating measurements for body regions to be optimized, using suitable regions of the reference phantom.

16. The method as claimed in claim 15, wherein the varied recording parameters comprise varied flip angles, partial Fourier factors/trajectories, varied echo time, varied repetition time (TR) train, and/or varied echo train.

17. A non-transitory computer-readable storage medium with an executable program stored thereon, that when executed, instructs a processor to perform the method of claim 1.

18. A computer program product having a computer program which is directly loadable into a memory of a controller of the magnetic resonance tomography system, when executed by the controller, causes the magnetic resonance tomography system to perform the method as claimed in claim 1.

19. A Magnetic Resonance Fingerprinting (MRF) processor for controlling a magnetic resonance tomography system for an MRF measurement, the MRF processor comprising:
a dictionary group generator and/or a data interface; the dictionary group generator being configured to create a dictionary group, and the data interface being configured to receive the dictionary group supplied thereto, wherein the dictionary group includes at least two dictionaries each containing a multiplicity of different intensity profiles of image dots from a series of magnetic resonance tomography (MRT) recordings with a specific sampling scheme;
a preliminary recorder configured to prepare a preliminary recording of MRT measurements;
a determiner configured to determine and define a sampling scheme based on the preliminary recording;
a selector configured to select a dictionary from the at least two dictionaries of the dictionary group based on the preliminary recording; and an evaluator configured to perform an MRF measurement using the defined sampling scheme and an MRF evaluation based on the selected dictionary.

20. A controller configured to control the magnetic resonance tomography system, the controller comprising the MRF processor as claimed in claim 19.

21. A magnetic resonance tomography system comprising the controller as claimed in claim 20.

22. A method for producing a magnetic resonance tomography system, the method comprising:
   setting up the magnetic resonance tomography system;
   providing a number of reference phantoms in the magnetic resonance tomography system;
   preparing a multiplicity of magnetic resonance tomography (MRT) recordings, from the number of reference phantoms, with varying recording parameters;
   creating a plurality of dictionaries of pixel-based intensity profiles of the MRT recordings, a specific sampling scheme being used for creation of each of the dictionaries; and
   saving the plurality of dictionaries as a dictionary group, in a memory of the magnetic resonance tomography system, together with: information for each dictionary of the plurality of dictionaries indicating sampling scheme was used for the corresponding dictionary, and information indicating an intended examination region of the corresponding dictionary.

23. The method as claimed claim 1, wherein the preparing the preliminary recording of the MRT measurements comprises performing a prescan to record the MRT measurements before the MRF measurement is performed.

* * * * *